United States Patent [19]

Ladner

[11] Patent Number: 4,459,409
[45] Date of Patent: Jul. 10, 1984

[54] PROCESS FOR THE PREPARATION OF 2,3-QUINOLINEDICARBOXYLIC ACIDS

[75] Inventor: David W. Ladner, Hamilton Square, N.J.

[73] Assignee: American Cyanamid Company, Stamford, Conn.

[21] Appl. No.: 381,827

[22] Filed: May 25, 1982

[51] Int. Cl.$^3$ .......................................... C07D 215/54
[52] U.S. Cl. ................................... 546/170; 546/168
[58] Field of Search ......................................... 546/170

[56] References Cited

U.S. PATENT DOCUMENTS 2,109,954  3/1938  Biswell et al. ...................... 546/170

OTHER PUBLICATIONS

Moriconi et al., J. Am. Chem. Soc., 86, pp. 38–46 (1964).

Primary Examiner—Paul M. Coughlan, Jr.
Assistant Examiner—D. B. Springer
Attorney, Agent, or Firm—H. G. Jackson

[57] ABSTRACT

There is provided a novel process for the preparation of a substituted or unsubstituted 2,3-quinolinedicarboxylic acid, utilizing as the starting material, 2-methyl-3-quinolinecarboxylic acid or 3-methyl-2-quinolinecarboxylic acid or the alkyl ester of either of the above compounds.

7 Claims, No Drawings

PROCESS FOR THE PREPARATION OF 2,3-QUINOLINEDICARBOXYLIC ACIDS

SUMMARY OF THE INVENTION

This invention relates to a method for the preparation of a formula (I) substituted or unsubstituted 2,3-quinolinedicarboxylic acid having the structure:

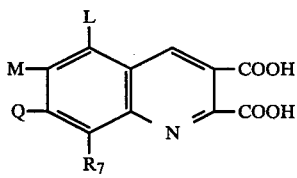

(I)

wherein L, M, Q and $R_7$, each represent members selected from the group consisting of H, halogen (Cl, Br, F or I), $C_1$–$C_4$ alkyl, $C_1$–$C_4$ alkoxy, $C_1$–$C_4$ alkylsulfonyl, halo ($C_1$–$C_4$)alkyl, $NO_2$, CN, phenyl, phenoxy, difluoromethoxy, chlorophenyl or phenoxy substituted with one Cl, $CF_3$, $NO_2$ or $CH_3$ group, with the proviso that only one of L, M, Q and $R_7$, may represent a substituent other than hydrogen, halogen, $C_1$–$C_4$ alkyl or $C_1$–$C_4$ alkoxy.

The method of the present invention involves the oxidation of the methyl function of a formula (II) 2-methyl-3-quinolinecarboxylic acid or formula (IIa) 3-methyl-2-quinolinecarboxylic acid. It also involves the oxidation of the methyl function and the simultaneous hydrolysis of the ester function of a formula (II) alkyl-2-methyl-3-quinolinecarboxylate or a formula (IIa) alkyl 3-methyl-2-quinolinecarboxylate. The above-said formula (II) and (IIa) acids and esters have the structures illustrated below:

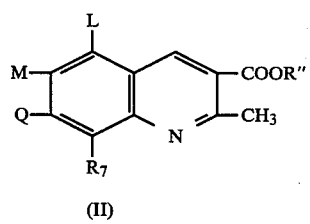

(II)

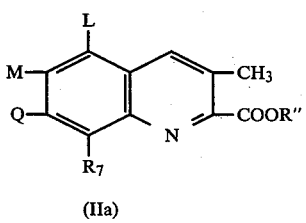

(IIa)

wherein L, M, Q and $R_7$ are as described above and R" is hydrogen or $C_1$–$C_4$ alkyl.

In accordance with the process of this invention, the formula (II) 2-methyl-3-quinolinecarboxylic acid or alkyl 2-methyl-3-quinolinecarboxylate or formula (IIa) 3-methyl-2-quinolinecarboxylic acid or alkyl 3-methyl-2-quinolinecarboxylate, is admixed with a sufficient amount of water to give a 0.02 to 1.0M solution of said compound in the water. To this solution is added 5–15% by weight of aqueous alkali metal hydroxide such as sodium or potassium hydroxide. The thus-prepared mixture is stirred to provide an essentially homogeneous mixture. In practice, it has been found beneficial, although not essential for the formula (II) starting material to have some solubility in the reaction medium, either initially or after saponification of the functional group R". The reaction mixture is then treated with from 3.0 to 4.0 molar equivalents (preferably up to 1 molar equivalent excess) of nickel peroxide. Addition of the nickel peroxide to the mixture can be made in small increments or all at once. However, the temperature of the reaction mixture should be maintained at from 0° to 30° C., and the mixture should be stirred until the oxidation and hydrolysis are essentially complete. At the end of the reaction time, no starting material is detectable, and the insoluble inorganic materials are removed by decantation, filtration, or the like. The filtrate is then acidified to pH 2 with hydrochloric acid to give the formula (I) quinoline-2,3-dicarboxylic acid where L, M, Q and $R_7$, are as described above and has the structure:

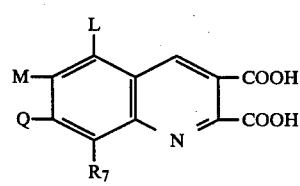

Preparation of the formula (II) starting material, essential for the above-described reaction, is accomplished by reaction of an appropriately substituted formula (III) aniline wherein L, M, Q and $R_7$ are as described above, with a keto-ester depicted as formula (IV) wherein R" is $C_1$–$C_4$ alkyl. This reaction is optionally conducted in the presence of an organic sulfonic acid such as p-toluenesulfonic acid hydrate, camphorsulfonic acid or the like, in the presence of an organic solvent such as toluene, xylene, benzene or the like, at a temperature of from 20° to 110° C., and preferably 100° to 110° C. The reaction yields the β-anilino-α, β-unsaturated ester of formula (V). The thus-formed β-anilino-α,β-unsaturated ester of formula (V) is then reacted with an immonium salt depicted by formula $Cl-CH=N^{\oplus}-(R''')_2 \cdot Cl^{\ominus}$ (VI) wherein R''' is $C_1$–$C_6$ alkyl or (VIa) $Cl-CH=N^{\oplus}(CH_2)_{n'} \cdot Cl^{\ominus}$ wherein n' is an integer selected from 4 or 5. While the anion in formula VI and VIa are shown as Cl—, it should be recognized that when $POCl_3$ is used to prepare the Vilsmeier reagent the anion is $PO_2Cl_2$—. This reaction is conducted in the presence of a low boiling chlorinated hydrocarbon solvent such as methylene chloride or dichloroethane at a temperature between about 40° and 90° C., for a period of time sufficient to essentially complete the reaction and yield the formula (II) alkyl 2-methyl-3-quinolinecarboxylate, which may be used as the starting material for the preparation of the formula (I) 2,3-quinolinedicarboxylic acid. If desired, the formula (II) ester may first be converted to the 2-methyl-3-quinolinecarboxylic acid and then the acid used as starting material for the preparation of the formula (I) 2,3-quinolinedicarboxylic acid.

Conversion of the alkyl 2-methyl-3-quinolinecarboxylate to the 2-methyl-3-quinolinecarboxylic acid, can be achieved by reaction of the formula (II) quinolinecarboxylate with alcoholic alkali metal hydroxide followed by acidification of the reaction mixture with hydrochloric acid.

The immonium salt formula (VI or VIa), utilized in the above cyclization reactions may be referred to as the Vilsmeier reagent. This reagent may be generated from a formamide (alkyl or phenyl) reaction with $POCl_3$, $COCl_2$, $ClCO-COCl$ or $SOCl_2$ in a chlorinated hydrocarbon solvent.

This process is graphically illustrated in Flow Diagram I below and is described in the application for United States Letters Patent of Robert Francis Doehner, Ser. No. 381,815, filed concurrently herewith and incorporated herein by reference thereto.

Following isolation, the formula (I) quinoline-2,3-dicarboxylic acid is heated to about 70° to 95° C. with an excess of acetic anhydride to yield the formula (IX) 2,3-quinolinedicarboxylic anhydride, having the structure:

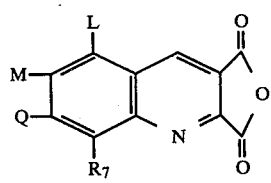

wherein L, M, Q and $R_7$ are as described above. A co-solvent such as pyridine or pyridine-dimethoxyethane may also be used in this reaction, but is not essential to obtain the desired product.

Reaction of the formula (IX) 2,3-quinolinedicarboxylic anhydride with a formula (X) aminocarboxamide or aminothiocarboxamide having the structure:

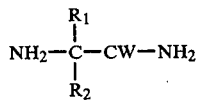

wherein $R_1$ is $C_1-C_4$ alkyl; $R_2$ is $C_1-C_4$ alkyl or $C_3-C_6$ cycloalkyl; and when $R_1$ and $R_2$ are taken together they may represent $C_3-C_6$ cycloalkyl optionally substituted with methyl; and W is sulfur or oxygen; is preferably carried out using equivalent amounts of the anhydride and carboxamide or thiocarboxamide in the presence of an inert organic solvent such as tetrahydrofuran, diethyl ether, or the like at a temperature between about 0° and 30° C. When the reaction is essentially complete, the solvent is evaporated, and the residue triturated with a solvent such as ethyl acetate to afford an isomeric mixture of the 3-quinolinecarboxylic acid and the quinaldic acid shown, respectively, as formula (XIa) having the structure:

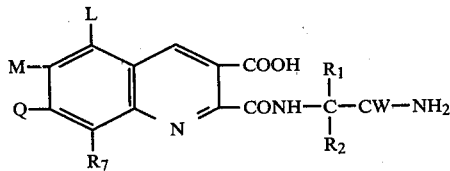

where L, M, Q, $R_7$, $R_1$, $R_2$ and W, are as described above; or formula (XIb) having the structure:

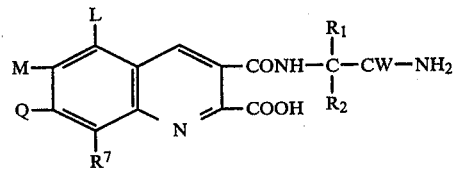

where L, M, Q, $R_7$, $R_1$ and $R_2$ and W, are as described above.

The thus-formed mixture is then heated to a temperature of from 25° to about 110° C. with about 2 to 10 molar equivalents of aqueous or aqueous alcoholic sodium or potassium hydroxide, preferably under a blanket of inert gas such as nitrogen. The mixture is cooled to about 25° C. and acidified to pH 2 to 4 with a strong mineral acid such as hydrochloric acid or sulfuric acid to give the herbicidally effective 2-(5,5-disubstituted-4-oxo-(or thiono)-2-imidazolin-2-yl)-3-quinolinecarboxylic acids, encompassed by formula (XII); wherein $R_1$ is $C_1-C_4$ alkyl; $R_2$ is $C_1-C_4$ alkyl or $C_3-C_6$ cycloalkyl; and when $R_1$ and $R_2$ are taken together they may represent $C_3-C_6$ cycloalkyl optionally substituted with methyl, and when $R_1$ and $R_2$ are not the same, the optical isomers thereof; W is O or S; and L, M, Q, and $R_7$ each represent members selected from the group consisting of hydrogen, halogen, $C_1-C_4$ haloalkyl, difluoromethoxy, nitro, phenyl, phenoxy or monosubstituted phenyl or phenoxy where the substituent is $C_1-C_4$ alkoxy; or halogen; with the proviso that only one of L, M, Q, or $R_7$ may represent a substituent other than hydrogen, halogen, $C_1-C_4$ alkyl or $C_1-C_4$ alkoxy. The above reactions are graphically illustrated in Flow Diagram I below and described in the application for United States Letters of Marinus Los, Ser. No. 382,041, filed concurrently herewith and incorporated herein by reference thereto.

FLOW DIAGRAM I

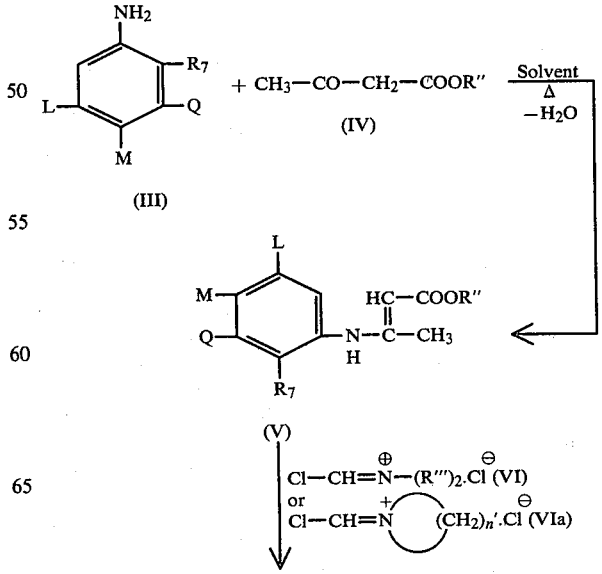

-continued
FLOW DIAGRAM I

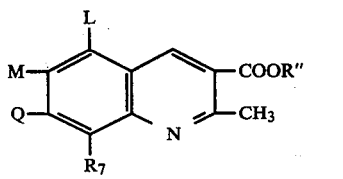

(II)

NaOH
H₂O
Nickel peroxide

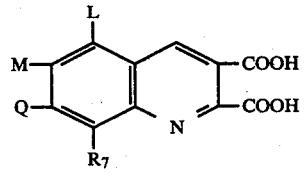

(I)

Ac₂O

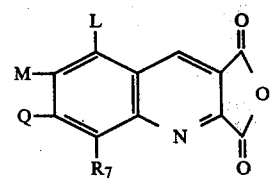

(IX)

$$NH_2-\underset{R_2}{\overset{R_1}{\underset{|}{\overset{|}{C}}}}-CW-NH_2$$

(X)

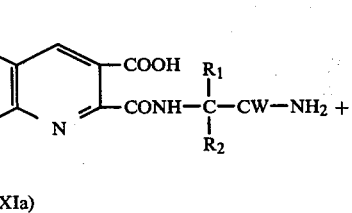

(XIa)

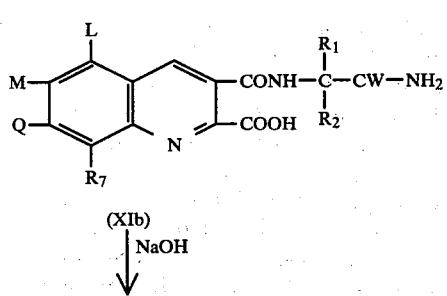

(XIb)

NaOH

-continued
FLOW DIAGRAM I

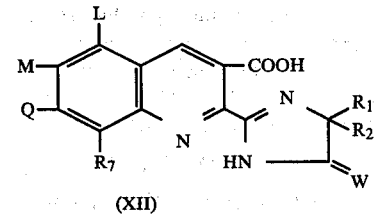

(XII)

The formula (XII) 2-(5,5-disubstituted-4-oxo-(or thiono)-2-imidazolin-2-yl)-3-quinolinecarboxylic acids are highly effective herbicidal agents useful for controlling a variety of annual and perennial monocotyledonous and dicotyledonous plants. These compounds are herbicidally effective for controlling weeds indigenous to both dry land and wet land areas. They are also useful as aquatic herbicides and are unique in their effectiveness in controlling the above-said plants when applied to the foliage thereof or to the soil or water containing seeds or other propagating organs of said plants such as tubers, rhizomes or stolons, at rates of from about 0.025 to 8.0 kg/ha, and preferably at rates from about 0.032 to 2.0 kg/ha.

For application to undesirable plants, these compounds can be formulated as wettable powders, emulsifiable concentrates, flowable liquids, granular formulations and the like, and applied as aqueous sprays or granular solids to the foliage of the plants or to the soil or water containing seeds or other propagating organs thereof.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butylcellosolve, methylacetate or the like and dispersing therein about 5% to 10% by weight of a nonionic surfactant such as alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of Ethyl-3-phenylaminobut-2-enoate

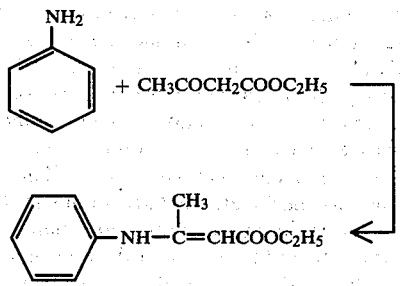

Aniline (0.20 mol) and ethylacetoacetate (0.20 mol) are mixed in toluene (200 ml) containing 0.04 g of p-toluenesulfonic acid-hydrate and heated at reflux under a water separator for 1 hour. The toluene is removed under vacuum to afford the ethyl-3-phenylaminobut-2-enoate which can be used as is for the preparation of the 3-quinolinecarboxylic acid, 2-methyl-, ethyl ester.

Following the above procedure and utilizing the appropriate keto ester and the appropriately substituted aniline, will yield the following compounds:

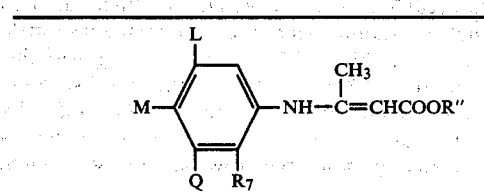

| L | M | Q | R$_7$ | R" |
|---|---|---|---|---|
| H | H | H | H | C$_2$H$_5$ |
| H | NO$_2$ | H | H | CH$_3$ |
| H | H | H | OCH$_3$ | CH$_3$ |
| H | CN | H | H | CH$_3$ |
| H | C$_6$H$_5$ | H | H | CH$_3$ |
| H | CF$_3$ | H | H | CH$_3$ |
| H | H | CH$_3$ | CH$_3$ | CH$_3$ |
| H | OCH$_3$ | H | H | CH$_3$ |
| H | CH$_3$ | CH$_3$ | H | CH$_3$ |
| OCH$_3$ | H | H | OCH$_3$ | C$_2$H$_5$ |
| H | C$_2$H$_5$ | H | H | CH$_3$ |
| H | Br | H | H | CH$_3$ |
| H | H | OC$_2$H$_5$ | H | CH$_3$ |
| H | C$_4$H$_9$ | H | H | CH$_3$ |
| H | OCHF$_2$ | H | H | CH$_3$ |

EXAMPLE 2

Preparation of Dimethyl 2,3-quinolinedicarboxylate

To a solution of dimethylformamide (DMF, 0.1 mol) in ethylenedichloride (EDC, 100 ml), cooled in an ice bath, is added dropwise with stirring phosphorous oxychloride (POCl$_3$, 0.10 mol). The resulting solution is stirred for one and one-half hours at room temperature and then cooled in an ice bath. To the cooled solution is then added, in small increments, a solution of dimethyl 3-phenylaminobut-2-ene-dioate in ethylene dichloride. The resulting mixture is thereafter heated to reflux for three hours, cooled, and washed with half saturated brine. The organic phase is separated from the aqueous phase and dried. The solvent is removed under vacuum, and the residue recrystallized from methanol to afford 18.2 g (0.074 mol) of dimethyl-2,3-quinolinedicarboxylate, mp 105°–106.5° C.

Using the above procedure and the appropriate 3-phenylaminobut-2-eneoate, yields the 2-methyl-3-quinolinecarboxylates reported below.

| L | M | Q | R$_7$ | R" |
|---|---|---|---|---|
| H | H | H | H | C$_2$H$_5$ |
| H | H | H | H | C$_2$H$_5$ |
| H | NO$_2$ | H | H | CH$_3$ |
| H | H | H | OCH$_3$ | CH$_3$ |
| H | CN | H | H | CH$_3$ |
| H | C$_6$H$_5$ | H | H | CH$_3$ |
| H | CF$_3$ | H | H | CH$_3$ |
| H | H | CH$_3$ | CH$_3$ | CH$_3$ |
| H | OCH$_3$ | H | H | CH$_3$ |
| H | CH$_3$ | CH$_3$ | H | CH$_3$ |
| OCH$_3$ | H | H | OCH$_3$ | C$_2$H$_5$ |
| H | OC$_6$H$_5$ | H | H | CH$_3$ |
| H | C$_2$H$_5$ | H | H | CH$_3$ |
| H | C$_4$H$_9$ | H | H | CH$_3$ |
| H | Br | H | H | CH$_3$ |
| H | H | OC$_2$H$_5$ | H | CH$_3$ |
| H | OCHF$_2$ | H | H | CH$_3$ |
| H | Cl | H | H | CH$_3$ |

EXAMPLE 3

Preparation of 3-methyl-2-quinolinecarboxylic acid

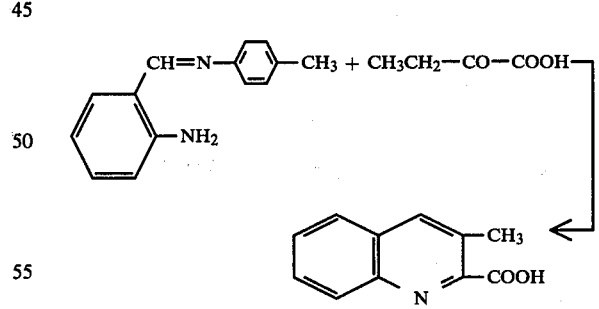

To 100 ml of absolute ethanol is added 4.0 g (0.02 mol) of N-o-aminobenzylidine-p-toluidine, 10 drops of piperidine and 3.89 g (0.04 mol) of 2-ketobutyric acid. The mixture is stirred and heated to reflux temperature for three hours, then cooled and concentrated in vacuo. The residue is taken up in 10% aqueous sodium carbonate solution and washed with an ether/petroleum ether (2:1) solution. Acidification of the aqueous layer followed by concentration in vacuo to 15 ml gives an off-white solid having a melting point of 141°–142° C.

EXAMPLE 4

Preparation of 2,3-quinolinedicarboxylic acid

Three grams of 2-methylquinoline-3-carboxylic acid (0.012 mol of 3.5 hydrate) is dissolved in 100 ml 15% sodium hydroxide solution and an additional 100 ml $H_2O$ is added. The mixture becomes homogeneous. At room temperature is added, all at once, 12.0 g nickel peroxide, (0.044 mol, 3.6 eq, 20% excess) and the mixture is stirred magnetically for 12 hours. The insolubles are removed by vacuum filtration and washed with water. The filtrate is acidified to pH 2 and a solid fluffy precipitate forms. It is filtered and dried to give 2.48 g of quinoline-2,3-dicarboxylic acid which is hydrated with 1.3 moles $H_2O$/mole compound as determined by NMR. Additional product is isolated from the aqueous filtrate by concentration and filtration. This brings the total actual product yield to 2.88 g of product having a melting point of 271°–277° C. Product yield is essentially quantitative.

Following the above procedure but substituting the appropriate substituted 2-methylquinoline-3-carboxylic acid for 2-methylquinoline-3-carboxylic acid will yield the following substituted 2,3-quinolinedicarboxylic acids.

| L | M | Q | $R_7$ | mp °C. |
|---|---|---|---|---|
| H | $NO_2$ | H | H | 295–297 (dec.) |
| H | H | H | $OCH_3$ | 270–275 |
| H | $CF_3$ | H | H | 165–167 |
| H | CN | H | H | >300 |
| H | $C_6H_5$ | H | H | >300 |
| H | H | $CH_3$ | $CH_3$ | 148–150 |
| H | $OCH_3$ | H | H | — |
| $OCH_3$ | H | H | $OCH_3$ | 274–276 |
| H | $C_2H_5$ | H | H | 190–195 |
| H | $C_4H_9$-n | H | H | — |
| H | $OC_6H_5$ | H | H | — |
| H | $OCHF_2$ | H | H | 226– |
| H | H | $OC_2H_5$ | H | 197–198 (dec.) |
| H | Br | H | H | 254–255 |
| H | Cl | H | H | 251–253 |

EXAMPLE 5

Preparation of 2,3-quinolinedicarboxylic acid

Following the procedure of Example 4 but substituting 3-methylquinoline-2-carboxylic acid for 2-methylquinoline-3-carboxylic acid affords the title compound, mp 271°–277° C., in 70% yield.

EXAMPLE 6

Preparation of 2,3-quinolinedicarboxylic acid

2-Methylquinoline-3-carboxylic acid (1.25 g, 0.005 mol) is dissolved in a mixture of 40 ml of water and 20 ml of 15% sodium hydroxide. To this mixture is added nickel (II) chloride (hexahydrate) (0.23 g, 0.001 mol). The resulting mixture is stirred while 20 ml of 5.25% sodium hypochlorite solution, in 30 ml $H_2O$, is added at the rate of 5–7 drops per minute. After stirring for 14 hours, the solids are removed by filtration, and the filtrate acidified to pH 2 with HCl and concentrated to a volume of 25 ml in vacuo. A yellow solid separates which weighs 0.70 g and is recovered starting material. Further concentration of the aqueous phase gives 0.37 g of the 2,3-quinolinedicarboxylic acid, mp 271°–277° C.

EXAMPLE 7

Preparation of 2,3-quinolinedicarboxylic anhydride

A mixture of 2,3-quinolinedicarboxylic acid-trihydrate (0.141 mol) in acetic anhydride (125 ml) is heated at 85° C. for ½ hour and then at 100° C. for 1 hour. The reaction mixture is then cooled to room temperature, filtered and the solids washed with ethyl ether to afford the desired 2,3-quinolinedicarboxylic anhydride, mp 225°–228° C.

Utilizing the above procedure but substituting the appropriately substituted 2,3-quinolinedicarboxylic acid for 2,3-quinolinedicarboxylic acid-trihydrate, yields the following substituted 2,3-quinolinedicarboxylic anhydrides.

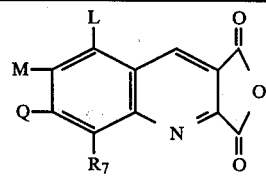

| L | M | Q | $R_7$ | mp °C. |
|---|---|---|---|---|
| H | $OC_6H_5$ | H | H | 187–188 |
| H | $NO_2$ | H | H | 225–228 (dec) |
| H | $C_6H_5$ | H | H | 258.5–261 |
| H | H | $CH_3$ | $CH_3$ | 270–272 |
| H | $OCH_3$ | H | H | 208–210 |
| H | $CH_3$ | $CH_3$ | H | |
| H | CN | H | H | 190–192 |
| H | H | H | $OCH_3$ | |
| H | $C_2H_5$ | H | H | 212–214 |
| H | $C_4H_9$-n | H | H | ~160–210 |
| $OCH_3$ | H | H | H | 266–267 |
| H | $CF_3$ | H | H | 157–159 |
| H | $OCHF_2$ | H | H | 157.5–158.5 |
| H | Cl | H | H | 243–245 |
| H | H | $OC_6H_5$ | H | 222–224 |

EXAMPLE 8

Preparation of 2-[(1-carbamoyl-1,2-dimethylpropyl)carbamoyl]-3-quinolinecarboxylic acid A solution of 2,3-quinolinedicarboxylic anhydride (0.037 mol) in tetrahydrofuran (THF, 250 ml) is stirred at 5° C. under a drying tube, and a solution of 2-amino-2,3-dimethylbutyramide (0.037 mol) in THF (50 ml) added thereto, in small increments, over a 15 minute period. The reaction mixture is allowed to warm slowly to room temperature for an extended period of time, i.e. about 17 hours. The solvent is evaporated in vacuo to afford a gummy residue, which is triturated with hot ethyl acetate (400 ml) and then filtered to afford the desired 2-[(1-carbamoyl-1,2-dimethylpropyl)carbamoyl]-3-quinolinecarboxylic acid, mp 172.5°–173.5° C.

Utilizing the above procedure but substituting the appropriately substituted 2,3-quinolinedicarboxylic anhydride for 2,3-quinolinedicarboxylic anhydride yields are following 2-[(1-carbamoyl-1,2-dimethylpropyl)-carbamoyl]-1,2-dimethylpropyl)carbamoyl]-3-quinolinecarboxylic acids.

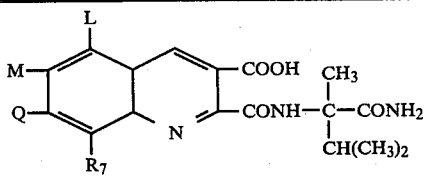

| L | M | Q | R$_7$ | mp °C. |
|---|---|---|---|---|
| H | OC$_6$H$_5$ | H | H | 189-190 |
| H | NO$_2$ | H | H | 225-227 (dec) |
| H | H | H | OCH$_3$ | foam |
| H | CF$_3$ | H | H | 222-224 |
| H | CN | H | H | |
| H | C$_6$H$_5$ | H | H | 189.5-192 |
| H | H | CH$_3$ | CH$_3$ | 246-250 |
| H | OCH$_3$ | H | H | |
| H | CH$_3$ | CH$_3$ | H | |
| H | C$_2$H$_5$ | H | H | 198-199 |
| H | C$_4$H$_9$ | H | H | |
| OCH$_3$ | H | H | OCH$_3$ | 209-209.5 |
| H | CF$_3$ | H | H | 222-224 |
| H | OCHF$_2$ | H | H | 194-196 |
| H | Br | H | H | 234-235 |
| H | Cl | H | H | 225-226 (dec) |
| H | H | OC$_2$H$_5$ | H | 194.5-195.5 |

EXAMPLE 9

Preparation of 2-(5-isopropyl-5-methyl-4-oxo-2-imidazolin-2-yl)-3-quinolinecarboxylic acid A solution of 2-[(1-carbamoyl-1,2-dimethylpropyl)-carbamoyl]-3-quinolinecarboxylic acid (0.152 mol), in water (50 ml) containing sodium hydroxide (0.06 mol) is heated at 75° to 80° C. for 2 hours. The solution is cooled in an ice bath and acidified with concentrated hydrochloric acid, added in small increments. The resulting precipitate is filtered, washed with water, air dried, and recrystallized from acetone to afford the 2-(5-isopropyl-5-methyl-4-oxo-2-imidazolin-2-yl)-3-quinolinecarboxylic acid, mp 239°-243.5° C.

Utilizing the above procedure and substituting the appropriate 3-quinolinecarboxylic acid for 2-[(1-carbamoyl-1,2-dimethylpropyl)carbamoyl]-3-quinolinecarboxylic acid yields the compounds illustrated below.

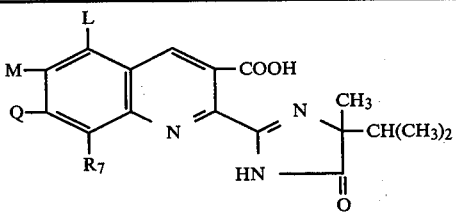

| L | M | Q | R$_7$ | mp °C. |
|---|---|---|---|---|
| H | NO$_2$ | H | H | 241.5-242 |
| H | OC$_6$H$_5$ | H | H | 223 |
| H | H | H | OCH$_3$ | 258.5-261 |
| H | CF$_3$ | H | H | 215-218 |
| H | C$_6$H$_5$ | H | H | 209.5-212 |
| H | CH$_3$ | CH$_3$ | H | 238-240 |
| OCH$_3$ | H | H | OCH$_3$ | 249-250 |
| H | C$_2$H$_5$ | H | H | 179.5-180.5 |
| H | C$_4$H$_9$ | H | H | 149-150.5 |
| H | H | CH$_3$ | CH$_3$ | 238-240 |
| H | OCHF$_2$ | H | H | 206-209 |

-continued

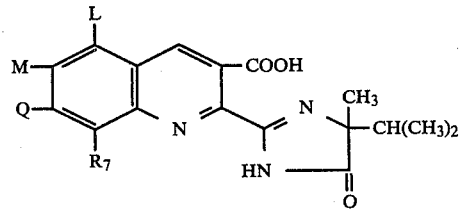

| L | M | Q | R$_7$ | mp °C. |
|---|---|---|---|---|
| (+) H | Cl | H | H | |

EXAMPLE 10

Post-Emergence Herbicidal Evaluation of Test Compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantity to provide the equivalent of about 0.016 kg of 10 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From 4 to 5 weeks after treatment, the seedling plants, are examined and rated according to the rating system provided below. The data obtained are recorded in Table I below.

| Rating System | % Difference in Growth from the Check* |
|---|---|
| 0 No effect | 0 |
| 1 Possible effect | 1-10 |
| 2 Slight effect | 11-25 |
| 3 Moderate effect | 26-40 |
| 5 Definite injury | 41-60 |
| 6 Herbicidal effect | 61-75 |
| 7 Good Herbicidal effect | 76-90 |
| 8 Approaching complete kill | 91-99 |
| 9 Complete kill | 100 |
| 4 Abnormal growth, that is, a definite physiological malformation but with an over-all effect less than a 5 on the rating scale. | |

In most cases the data are for a single test, but in several instances, they are average values obtained from more than one test.

The data are average values obtained from more than on test.

| Plant Species Used | |
|---|---|
| Barnyardgrass | (Eschinochloa crusgalli) |
| Green foxtail | (Setaria viridis) |
| Purple nutsedge | (Cyperus rotundus L.) |
| Wild oats | (Avena fatua) |
| Quackgrass | (Agropyron repens) |
| Field bindweed | (Convolvulus arvensis L.) |
| Cocklebur | (Xanthium pensylvanicum) |
| Morningglory | (Ipomoea purpurea) |

Plant Species Used

| | |
|---|---|
| Ragweed | (*Ambrosia artemisiifolia*) |
| Velvetleaf | (*Abutilon theophrasti*) |
| Barley | (*Hordeum vulgare*) |
| Corn | (*Zea mays*) |
| Rice | (*Oryza sativa*) |
| Soybean | (*Glycine max*) |
| Sunflower | (*Helianthus annus*) |
| Wheat | (*Triticum aestivum*) |

TABLE I

POST-EMERGENCE TESTS - RATES IN KG/HA

| Compound | RATE | BARN-YARDGR | GREEN FOX | P NUT-SEDGE | WILD OATS | QUACK GRASS | FLD BINDWD | MRNGLRY SP | RAG-WEED | VELVET-LEAF |
|---|---|---|---|---|---|---|---|---|---|---|
| 2-(5-Isopropyl-5-methyl-4-oxo-2-imidazolin-2-yl)-3-quinolinecarboxylic acid | 8.000 | 9.0 | 9.0 | 9.0 | 9.0 | 9.0 | 9.0 | 9.0 | | 9.0 |
| | 4.000 | 9.0 | 9.0 | 9.0 | 9.0 | 9.0 | 9.0 | 8.5 | 9.0 | 9.0 |
| | 2.000 | 9.0 | 9.0 | 8.5 | 9.0 | 9.0 | 9.0 | 8.3 | 8.5 | 9.0 |
| | 1.000 | 9.0 | 9.0 | 8.3 | 9.0 | 8.9 | 8.7 | 8.3 | 8.8 | 8.6 |
| | .800 | 9.0 | 8.8 | 6.8 | | 8.8 | 8.8 | 6.8 | 8.0 | 8.3 |
| | .500 | 8.9 | 8.9 | 7.6 | 9.0 | 8.6 | 8.3 | 7.7 | 8.4 | 7.7 |
| 2-(5-Isopropyl-5-methyl-4-oxo-2-imidazolin-2-yl)-6-nitro-3-quinolinecarboxylic acid | 1.000 | 9.0 | | 7.0 | 9.0 | 6.0 | 9.0 | 8.0 | 9.0 | 5.0 |
| | .500 | 9.0 | | 6.0 | 9.0 | 4.0 | 9.0 | 8.0 | 9.0 | 2.0 |
| | .250 | 9.0 | | 1.0 | 4.0 | 3.0 | 9.0 | 7.0 | 8.0 | 1.0 |
| | .125 | 4.0 | | 0.0 | 2.0 | 1.0 | 7.0 | | | 0.0 |
| | .063 | 1.0 | | 0.0 | 0.0 | 1.0 | 5.0 | 1.0 | 0.0 | 0.0 |
| 6-(Difluoromethoxy)-2-(5-isopropyl-5-methyl-4-oxo-2-imidazolin-2-yl)-3-quinolinecarboxylic acid | 1.000 | 9.0 | | 0.0 | 9.0 | 7.0 | 9.0 | 9.0 | 9.0 | 4.0 |
| | .500 | 8.0 | | 0.0 | 9.0 | 4.0 | 4.0 | 8.0 | | 3.0 |
| | .250 | 8.0 | | 0.0 | 9.0 | 4.0 | 1.0 | 7.0 | | 1.0 |
| | .125 | 6.0 | | 0.0 | 8.0 | 1.0 | | 6.0 | | 1.0 |
| | .063 | 5.0 | | 0.0 | 6.0 | 1.0 | 0.0 | 4.0 | | 0.0 |
| 2-(5-Isopropyl-5-methyl-4-oxo-2-imidazolin-2-yl)-8-methoxy-3-quinolinecarboxylic acid | 1.000 | 9.0 | | 7.0 | 9.0 | 6.0 | 2.0 | 3.0 | 8.0 | 9.0 |
| | .500 | 7.0 | | 4.0 | 9.0 | 5.0 | 1.0 | 1.0 | 8.0 | 9.0 |
| | .250 | 5.0 | | 2.0 | 9.0 | 4.0 | 1.0 | 1.0 | 7.0 | 9.0 |
| | .125 | 1.0 | | 0.0 | 8.0 | 3.0 | 1.0 | 0.0 | 6.0 | 9.0 |
| | .063 | 0.0 | | 0.0 | 8.0 | 1.0 | 0.0 | 0.0 | 1.0 | 0.0 |
| 2-(5-Isopropyl-5-methyl-4-oxo-2-imidazolin-2-yl)-6-(trifluoromethyl)-3-quinolinecarboxylic acid | 1.000 | 8.0 | | 0.0 | 9.0 | 6.0 | 2.0 | 2.0 | 9.0 | 3.0 |
| | .500 | 6.0 | | 0.0 | 8.0 | 4.0 | 1.0 | 1.0 | 8.0 | 1.0 |
| | .250 | 2.0 | | 0.0 | 7.0 | 1.0 | 0.0 | 1.0 | | 0.0 |
| | .125 | 1.0 | | 0.0 | 3.0 | 0.0 | 0.0 | 0.0 | | 0.0 |

POST-EMERGENCE TESTS - RATES IN KG/HA

| Compound | RATE | S BARLY LA | CORN FIELD | RICE, NATO | SOYBEAN WI | SUNFLR XXX | S WHEAT ER |
|---|---|---|---|---|---|---|---|
| 2-(5-Isopropyl-5-methyl-4-oxo-2-imidazolin-2-yl)-3-quinolinecarboxylic acid | 8.000 | | | | 0.5 | | |
| | 4.000 | | 9.0 | 9.0 | 0.0 | 9.0 | 9.0 |
| | 2.000 | | 9.0 | 9.0 | 0.1 | 9.0 | 9.0 |
| | 1.000 | 9.0 | 9.0 | 8.7 | 2.6 | 9.0 | 8.9 |
| | .800 | | | | 4.0 | | |
| | .500 | 9.0 | 9.0 | 8.3 | 2.3 | 9.0 | 8.8 |
| 2-(5-Isopropyl-5-methyl-4-oxo-2-imidazolin-2-yl)-6-nitro-3-quinolinecarboxylic acid | 1.000 | | 8.0 | 5.0 | | 8.0 | 9.0 |
| | .500 | | 8.0 | 4.0 | | 7.0 | 7.0 |
| | .250 | | 6.0 | 1.0 | | 6.0 | 3.0 |
| | .125 | | 7.0 | 1.0 | | 5.0 | 2.0 |
| | .063 | | 1.0 | 1.0 | | 5.0 | 0.0 |
| 6-(Difluoromethoxy)-2-(5-isopropyl-5-methyl-4-oxo-2-imidazolin-2-yl)-3-quinolinecarboxylic acid | 1.000 | | 9.0 | 7.0 | | 9.0 | 9.0 |
| | .500 | | 9.0 | 6.0 | | 9.0 | 9.0 |
| | .250 | | 9.0 | 5.0 | | 9.0 | 9.0 |
| | .125 | | 9.0 | 4.0 | | 9.0 | 7.0 |
| | .063 | | 9.0 | 2.0 | | 9.0 | 6.0 |
| 2-(5-Isopropyl-5-methyl-4-oxo-2-imidazolin-2-yl)-8-methoxy-3-quinolinecarboxylic acid | 1.000 | | 9.0 | 6.0 | | 9.0 | 9.0 |
| | .500 | | 9.0 | 5.0 | | 9.0 | 9.0 |
| | .250 | | 9.0 | 5.0 | | 9.0 | 9.0 |
| | .125 | | 9.0 | 4.0 | | 9.0 | 5.0 |
| | .063 | | 9.0 | 3.0 | | 9.0 | 3.0 |
| 2-(5-Isopropyl-5-methyl-4-oxo-2-imidazolin-2-yl)-6-(trifluoromethyl)-3-quinolinecarboxylic acid | 1.000 | | 8.0 | 5.0 | | 9.0 | 9.0 |
| | .500 | | 7.0 | 5.0 | | 9.0 | 6.0 |
| | .250 | | 7.0 | 2.0 | | 9.0 | 5.0 |
| | .125 | | 7.0 | 1.0 | | 9.0 | 2.0 |

EXAMPLE 11

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredients of the present invention is evident from the test results which are recorded in Table XII below. Where more than one test is involved for a given compound, the data are averaged.

TABLE II

| | | PRE-EMERGENCE TESTS - RATES IN KG/HA | | | | | | | | |
|---|---|---|---|---|---|---|---|---|---|---|
| Compound | RATE | BARN-YARDGR | GREEN FOX | P NUT-SEDGE | WILD OATS | QUACK GRASS | FLD BINDWD | MRGNLRY SP | RAG-WEED | VELVET-LEAF |
| 2-(5-Isopropyl-5-methyl-4-oxo-2-imidazolin-2-yl)-3-quinolinecarboxylic acid | 8.000 | 9.0 | 9.0 | 9.0 | 9.0 | 9.0 | 9.0 | 8.0 | 9.0 | 8.0 |
| | 4.000 | 9.0 | 9.0 | 9.0 | 9.0 | 9.0 | 9.0 | 9.0 | 9.0 | 9.0 |
| | 1.000 | 9.0 | 9.0 | 9.0 | 9.0 | 9.0 | 9.0 | 9.0 | 9.0 | 8.8 |
| | .500 | 8.8 | 9.0 | 9.0 | 8.9 | 9.0 | 9.0 | 8.5 | 8.9 | 8.5 |
| | .250 | 8.3 | 8.8 | 9.0 | 8.6 | 9.0 | 9.0 | 8.0 | 7.9 | 8.0 |
| 2-(5-Isopropyl-5-methyl-4-oxo-2-imidazolin-2-yl)-6-nitro-3-quinolinecarboxylic acid | 4.000 | 9.0 | 9.0 | 8.0 | 9.0 | 9.0 | 9.0 | 9.0 | 8.0 | 9.0 |
| | 1.000 | 9.0 | 9.0 | 9.0 | 9.0 | 9.0 | 9.0 | 9.0 | 8.0 | 7.0 |
| | .500 | 8.5 | 8.0 | 7.0 | 7.0 | 9.0 | 9.0 | 8.5 | 7.5 | 6.0 |
| | .250 | 9.0 | | 3.0 | 8.0 | 9.0 | 9.0 | 8.0 | 9.0 | 4.0 |
| | .125 | 6.0 | | 3.0 | 3.0 | 9.0 | 8.0 | 5.0 | 2.0 | 4.0 |
| 6-(Difluoromethoxy)-2-(5-isopropyl-5-methyl-4-oxo-2-imidazolin-2-yl)-3-quinolinecarboxylic acid | .500 | 9.0 | | 2.0 | 9.0 | 9.0 | 9.0 | 9.0 | 9.0 | 8.0 |
| | .250 | 5.0 | | 1.0 | 9.0 | 9.0 | 9.0 | 9.0 | 9.0 | 7.0 |
| | .125 | 4.0 | | 0.0 | 9.0 | 9.0 | 7.0 | 8.0 | 9.0 | 5.0 |
| | .063 | 0.0 | | 0.0 | 6.0 | 7.0 | 2.0 | 6.0 | 9.0 | 3.0 |
| 2-(5-Isopropyl-5-methyl-4-oxo-2-imidazolin-2-yl)-8-methoxy-3-quinolinecarboxylic acid | .500 | 7.0 | | 9.0 | 9.0 | 9.0 | 9.0 | 7.0 | 7.0 | 7.0 |
| | .250 | 7.0 | | 8.0 | 9.0 | 9.0 | 9.0 | 6.0 | 7.0 | 6.0 |
| | .125 | 3.0 | | 7.0 | 9.0 | 9.0 | 6.0 | 3.0 | 1.0 | 2.0 |
| | .063 | 2.0 | | 7.0 | 3.0 | 9.0 | 4.0 | 1.0 | 0.0 | 2.0 |
| 2-(5-Isopropyl-5-methyl-4-oxo-2-imidazolin-2-yl)-6-(trifluoromethyl)-3-quinolinecarboxylic acid | .500 | 7.0 | | 0.0 | 9.0 | 9.0 | 9.0 | 8.0 | 9.0 | 5.0 |
| | .250 | 5.0 | | 0.0 | 8.0 | 4.0 | 9.0 | 1.0 | 8.0 | 2.0 |
| | .125 | 1.0 | | 0.0 | 8.0 | 1.0 | 0.0 | | 4.0 | 2.0 |

| | | PRE-EMERGENCE TESTS - RATES IN KG/HA | | | | | |
|---|---|---|---|---|---|---|---|
| Compound | RATE | S BARLY LA | CORN FIELD | RICE, NATO | SOYBEAN WI | SUNFLR XXX | S WHEAT ER |
| 2-(5-Isopropyl-5-methyl-4-oxo-2-imidazolin-2-yl)-3-quinolinecarboxylic acid | 8.000 | | | | | | |
| | 4.000 | | 9.0 | 9.0 | | 9.0 | 9.0 |
| | 1.000 | 9.0 | 9.0 | 9.0 | 6.5 | 9.0 | 9.0 |
| | .500 | 9.0 | 9.0 | 9.0 | 4.0 | 8.7 | 8.9 |
| | .250 | 9.0 | 8.8 | 9.0 | 3.6 | 8.6 | 8.6 |
| 2-(5-Isopropyl-5-methyl-4-oxo-2-imidazolin-2-yl)-6-nitro-3-quinolinecarboxylic acid | 4.000 | | 9.0 | 9.0 | | 9.0 | 9.0 |
| | 1.000 | | 9.0 | 9.0 | | 8.0 | 9.0 |
| | .500 | | 8.5 | 9.0 | | 8.0 | 8.5 |
| | .250 | | 9.0 | 9.0 | | 8.0 | 7.0 |
| | .125 | | 9.0 | 9.0 | | 7.0 | 5.0 |
| 6-(Difluoromethoxy)-2-(5-isopropyl-5-methyl-4-oxo-2-imidazolin-2-yl)-3-quinolinecarboxylic acid | .500 | | 9.0 | 9.0 | | 9.0 | 9.0 |
| | .250 | | 9.0 | 9.0 | | 9.0 | 8.0 |
| | .125 | | 9.0 | 8.0 | | 9.0 | 8.0 |
| | .063 | | 9.0 | 6.0 | | 9.0 | 7.0 |
| 2-(5-Isopropyl-5-methyl-4-oxo-2-imidazolin-2-yl)-8-methoxy-3-quinolinecarboxylic acid | .500 | | 9.0 | 9.0 | | 9.0 | 8.0 |
| | .250 | | 9.0 | 9.0 | | 9.0 | 7.0 |
| | .125 | | 9.0 | 8.0 | | 9.0 | 7.0 |
| | .063 | | 9.0 | 8.0 | | 8.0 | 3.0 |
| 2-(5-Isopropyl-5-methyl-4-oxo-2-imidazolin-2-yl)-6-(trifluoro- | .500 | | 8.0 | 9.0 | | 9.0 | 8.0 |
| | .250 | | 2.0 | 7.0 | | 9.0 | 7.0 |
| | .125 | | 2.0 | 5.0 | | 8.0 | 5.0 |

TABLE II-continued methyl)-3-quino-
linecarboxylic
acid

I claim:
1. A method for the preparation of a quinoline-2,3-dicarboxylic acid having the structure:

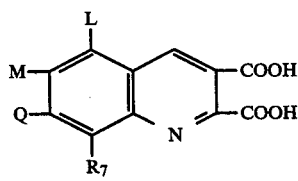

wherein L and Q are each hydrogen and M and $R_7$, are each H, $CF_3$, $NO_2$ or difluoromethoxy; with the proviso that only one of M and $R_7$, may represent a substituent other than hydrogen; comprising, admixing a compound having the structure:

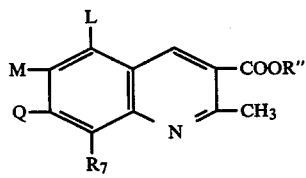

(II)

wherein R" is hydrogen or $C_1$–$C_4$ alkyl and L, M, Q and $R_7$, are as described above, or the compounds 3-methyl-2-quinolinecarboxylic acid or ethyl 3-methyl-2-quinolinecarboxylate with a sufficient quantity of water to give a 0.02 to 1.0M solution of said compound and adding thereto about 5–15% by weight of an aqueous alkali metal hydroxide; agitating the thus-formed mixture and admixing therewith from about 3.0 to 4.0 molar equivalents of nickel peroxide while maintaining the temperature of the reaction mixture at from 0° to 30° C. until oxidation of the methyl function, if R" is hydrogen, or oxidation of the methyl function and simultaneous hydrolysis of the ester function, if R" is $C_1$–$C_4$ alkyl, of the 2-methyl-3-quinolinecarboxylic acid; 3-methyl-2-quinolinecarboxylic acid, or the alkyl esters thereof, is essentially complete and, thereafter adjusting the pH of the reaction mixture to about pH 2, to obtain the quinoline-2,3-dicarboxylic acid.

2. A method according to claim 1 wherein the starting material is 2-methyl-3-quinolinecarboxylic acid.

3. A method according to claim 1 wherein the starting material is 3-methyl-2-quinolinecarboxylic acid.

4. A method according to claim 1 wherein the starting material is ethyl 2-methyl-3-quinolinecarboxylate.

5. A method according to claim 1 wherein the starting material is ethyl 3-methyl-2-quinolinecarboxylate.

6. A method according to claim 1 wherein the nickel II peroxide is used in an amount sufficient to provide from a slight to 1.0 mol excess based upon the molar equivalent of formula (II) quinolinecarboxylic acid or quinolinecarboxylate employed.

7. A method according to claim 1 wherein L, M, Q and $R_7$ are each hydrogen and R" is hydrogen or $C_1$–$C_4$ alkyl.

* * * * *